US012678597B2

(12) United States Patent
Kochan, II et al.

(10) Patent No.: US 12,678,597 B2
(45) Date of Patent: Jul. 14, 2026

(54) CATHETER HANGING SYSTEM

(71) Applicant: PAR Excellence Systems, Inc., Cincinnati, OH (US)

(72) Inventors: Thomas J. Kochan, II, Brighton, MI (US); Stanley S. Copeland, Saint Louisville, OH (US); Thaddeus MacKrell, Gross Pointe City, MI (US)

(73) Assignee: PAR Excellence Systems, Inc., Cincinnati, OH (US)

( * ) Notice: Subject to any disclaimer, the term of this patent is extended or adjusted under 35 U.S.C. 154(b) by 0 days.

(21) Appl. No.: 19/237,843

(22) Filed: Jun. 13, 2025

(65) Prior Publication Data

US 2025/0381369 A1 Dec. 18, 2025

Related U.S. Application Data

(60) Provisional application No. 63/659,653, filed on Jun. 13, 2024.

(51) Int. Cl.
| | |
|---|---|
| *G01G 19/42* | (2006.01) |
| *A47F 5/00* | (2006.01) |
| *A61M 25/02* | (2006.01) |
| *B25H 3/02* | (2006.01) |
| *G01G 21/00* | (2006.01) |
| *G07F 11/60* | (2006.01) |
| *G16H 40/40* | (2018.01) |
| *A47B 88/90* | (2017.01) |
| *G01G 19/414* | (2006.01) |
| *G16H 40/20* | (2018.01) |

(52) U.S. Cl.
CPC ............. *A61M 25/02* (2013.01); *A47B 88/90* (2017.01); *A47F 5/0006* (2013.01); *A61M 2025/028* (2013.01); *A61M 2209/082* (2013.01); *B25H 3/028* (2013.01); *G01G 19/4144* (2013.01); *G01G 19/42* (2013.01); *G01G 21/00* (2013.01); *G07F 11/60* (2013.01); *G16H 40/20* (2018.01); *G16H 40/40* (2018.01)

(58) Field of Classification Search
CPC . A47F 5/006; A47F 5/0006; A61M 2209/082; A61M 39/08; B25H 3/028; G01G 19/4144; G01G 19/42; G01G 21/00; G07F 11/60; G16H 40/40; G16H 40/20
See application file for complete search history.

(56) References Cited

U.S. PATENT DOCUMENTS

| | | | | |
|---|---|---|---|---|
| 1,132,190 | A | * | 3/1915 | Kohout ................ A47G 25/746 211/85.3 |
| 3,954,182 | A | * | 5/1976 | McEvers .............. A47G 25/746 211/94.01 |

(Continued)

*Primary Examiner* — William R Carpenter
*Assistant Examiner* — Robert F Allen
(74) *Attorney, Agent, or Firm* — FBT Gibbons LLP; Vance V. VanDrake, III; Alexander J. Johnson

(57) ABSTRACT

The present disclosure relates to a catheter hanging system for the purpose of storing catheters or similar medical devices while continuously weighing the catheters. The catheter hanging system includes a plurality of hooks, a plurality of load cells, and at least one circuit board. Each load cell of the plurality of load cells is configured to continuously measure a weight being applied to each hook of the plurality of hooks. The at least one circuit board is configured to receive signals from the plurality of load cells.

11 Claims, 12 Drawing Sheets

(56)          References Cited

U.S. PATENT DOCUMENTS

| | | | | |
|---|---|---|---|---|
| 5,000,407 | A * | 3/1991 | Juji | A61M 1/3646 |
| | | | | 280/47.35 |
| 5,022,538 | A * | 6/1991 | Richmond | A61M 5/1415 |
| | | | | 211/85.15 |
| 5,404,384 | A * | 4/1995 | Colburn | G06Q 10/087 |
| | | | | 377/6 |
| 5,745,366 | A * | 4/1998 | Higham | G07F 17/0092 |
| | | | | 700/242 |
| 5,790,409 | A * | 8/1998 | Fedor | G06M 7/04 |
| | | | | 700/214 |
| 5,805,456 | A * | 9/1998 | Higham | G07F 17/0092 |
| | | | | 312/215 |
| 5,848,593 | A * | 12/1998 | McGrady | G16H 20/13 |
| | | | | 128/897 |
| 5,905,653 | A * | 5/1999 | Higham | G07F 17/0092 |
| | | | | 700/242 |
| 5,971,593 | A * | 10/1999 | McGrady | G07F 17/0092 |
| | | | | 700/242 |
| 6,050,713 | A * | 4/2000 | O'Donnell | A61M 5/1411 |
| | | | | 362/418 |
| 6,976,595 | B1 * | 12/2005 | Geller | A47F 5/0838 |
| | | | | 211/124 |
| 7,685,026 | B1 * | 3/2010 | McGrady | G07F 11/64 |
| | | | | 705/28 |
| 10,732,026 | B1 * | 8/2020 | Danenberg | H05K 5/0073 |
| 10,746,589 | B1 * | 8/2020 | Danenberg | H05K 5/0073 |
| 10,809,122 | B1 * | 10/2020 | Danenberg | A47F 5/103 |
| 11,002,589 | B1 * | 5/2021 | Zhang | G01G 19/14 |
| 11,125,607 | B1 * | 9/2021 | Justice | G01G 19/42 |
| 2006/0190130 | A1 * | 8/2006 | Fedor | G07F 17/0092 |
| | | | | 700/236 |
| 2006/0259377 | A1 * | 11/2006 | Fedor | G06Q 20/208 |
| | | | | 705/28 |
| 2007/0262683 | A1 * | 11/2007 | Creed | A47B 67/00 |
| | | | | 312/311 |
| 2018/0336513 | A1 * | 11/2018 | Smith | G06Q 10/087 |
| 2019/0231467 | A1 * | 8/2019 | Grimsley | A61B 17/06133 |
| 2021/0030169 | A1 * | 2/2021 | Zhai | G01G 19/52 |
| 2021/0131857 | A1 * | 5/2021 | Trakhimovich | G01G 19/52 |
| 2021/0148750 | A1 * | 5/2021 | Trakhimovich | G01G 19/42 |
| 2021/0360889 | A1 * | 11/2021 | Smith | A01G 31/06 |
| 2021/0364338 | A1 * | 11/2021 | Grauberger | G01G 3/12 |
| 2022/0154495 | A1 * | 5/2022 | Manser | A47F 5/0876 |
| 2022/0221328 | A1 * | 7/2022 | Coffin | G01G 19/18 |
| 2022/0253796 | A1 * | 8/2022 | Kochan, II | B65G 1/137 |
| 2023/0389704 | A1 * | 12/2023 | Ratermann | A47B 97/00 |

* cited by examiner

104

108

316

CATHETER HANGING SYSTEM

CROSS REFERENCE TO RELATED APPLICATION

This application claims the priority benefit of U.S. Provisional Patent Application No. 63/659,653, filed Jun. 13, 2024, which is hereby incorporated herein by reference in its entirety.

BACKGROUND

In hospitals and large medical facilities, medical supplies must be stored, inventoried, and accessed. Inventories of medical supplies are often stored in a closet or storage room. At any given time, a variety of medical supplies must be readily available for use by a doctor, nurse, or other medical professional. For example, cabinets or racks may be used by a hospital to store instruments such as sutures.

A catheter hanging system is a specialized apparatus designed for organizing and storing catheters in medical settings. These systems typically consist of racks, hooks, or holders that allow medical professionals to hang catheters securely, while keeping them organized and accessible.

Catheter hanging systems maintain an efficient environment for medical procedures involving catheters, such as urinary catheters or intravenous lines. By providing a designated place for catheters, these systems help prevent contamination, reduce the risk of misplacement, and streamline the process of accessing the necessary equipment during patient care.

Catheter hanging systems come in various designs to accommodate different types and sizes of catheters. Some may be wall-mounted, while others are portable or attachable to medical carts or equipment. These systems enhance the safety and effectiveness of medical procedures involving catheters.

Catheter hanging systems are typically only compatible with specific storage units or fixtures designed to accommodate them. This results in a fixed configuration, making them less accommodating to various functions and changes in use.

DESCRIPTION OF DRAWINGS

While the specification concludes with claims which particularly point out and distinctly claim the disclosure, it is believed the present disclosure will be better understood from the following description of certain examples taken in conjunction with the accompanying examples and figures.

The figures are not intended to be limiting in any way, and it is contemplated that various embodiments of the present disclosure may be carried out in a variety of other ways. The accompanying figures incorporated in and forming a part of the specification show aspects of the present disclosure, and together with the description serve to explain the principles of the present disclosure; it being understood, however, that the present disclosure is not limited to what is shown in the figures.

DETAILED DESCRIPTION

The following description of certain examples of the present disclosure should not be used to limit the scope of the present disclosure. Other examples, features, aspects, embodiments, and advantages of the present disclosure will become apparent to those skilled in the art from the following description. As will be realized, the present disclosure is capable of other different and obvious aspects, all without departing from the present disclosure. Accordingly, the examples, figures, and descriptions should be regarded as illustrative in nature and not restrictive.

I. Exemplary Catheter Hanging System

The following description details a hanging system for use with a storage system for storing medical supplies such as catheters. While storage systems with baskets or cabinets may be used to store larger medical supplies, a hanging system may be used to vertically store smaller medical instruments such as urinary catheters or intravenous lines.

A catheter hanging system of the present disclosure may be integrated into storage units for medical devices. The catheter hanging system may be designed to accurately weigh items being hung on hooks. The catheter hanging system may include a plurality of load cells, wherein each load cell may be connected to a hook to continuously measure the weight of any item(s) hanging on that hook.

In some contexts, using a catheter hanging system that may be fixed into a storage unit presents challenges. A catheter hanging system only compatible with a specific storage unit designed to accommodate it may have a limited use. For instance, a hospital may want to rearrange the configuration of a storage unit that includes a catheter hanging system. Such changes or rearrangements may be difficult or impossible with a fixed catheter hanging system. Most available catheter hanging systems also require complex, time-consuming installation procedures. As technology advances, fixed catheter hanging systems may become outdated by becoming incompatible with newer storage units or software systems used to monitor the catheter hanging system. As will be discussed further below, the catheter hanging system of the present disclosure provides scalability and flexibility to help overcome these challenges.

Figure 1:
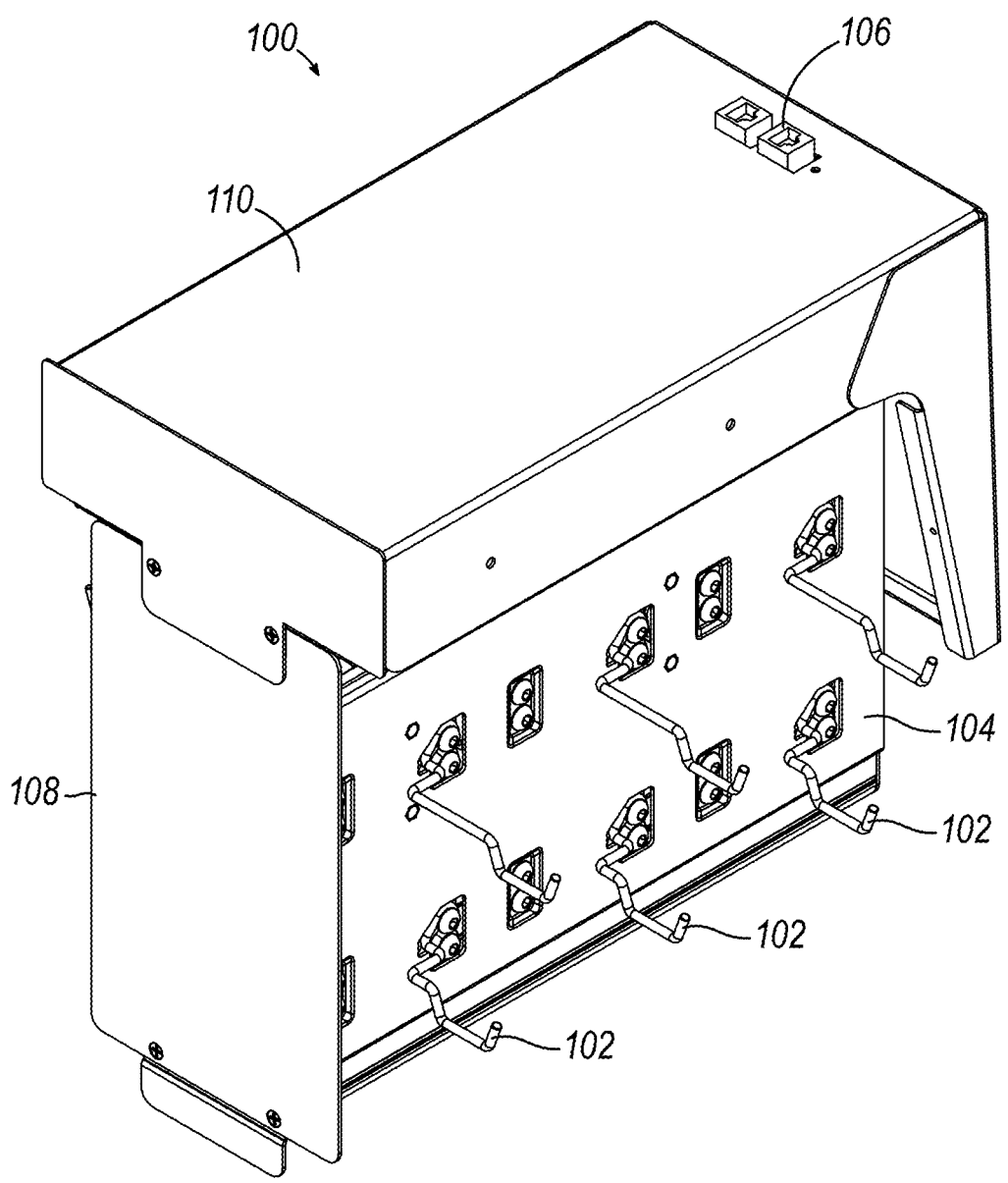
FIG. 1 is a perspective view of a catheter hanging system with a 12-scale configuration.

FIG. 1 shows a perspective view of a catheter hanging system (100) with a 12-scale configuration. In one or more embodiments, a catheter hanging system (100) includes a plurality of hooks (102) or pins to securely and vertically hang medical devices such as catheters. In some examples, hooks (102) may be made of metal. In other examples, hooks (102) may be made of plastic. When hanging a catheter on a hook (102), one may hang the catheter such that any label on the catheter can be facing out. Doing so can make identification of the catheter easier for medical professionals. In some examples, a unique item may be placed on each hook (102). As will be discussed in further detail below, each hook (102) may be associated with a load cell that measures the weight of medical instruments being carried on hook (102).

As will be discussed in greater detail below, in one or more embodiments, a chassis (104) may be configured to support the plurality of hooks (102) and load cells in a structured arrangement.

Figure 2:
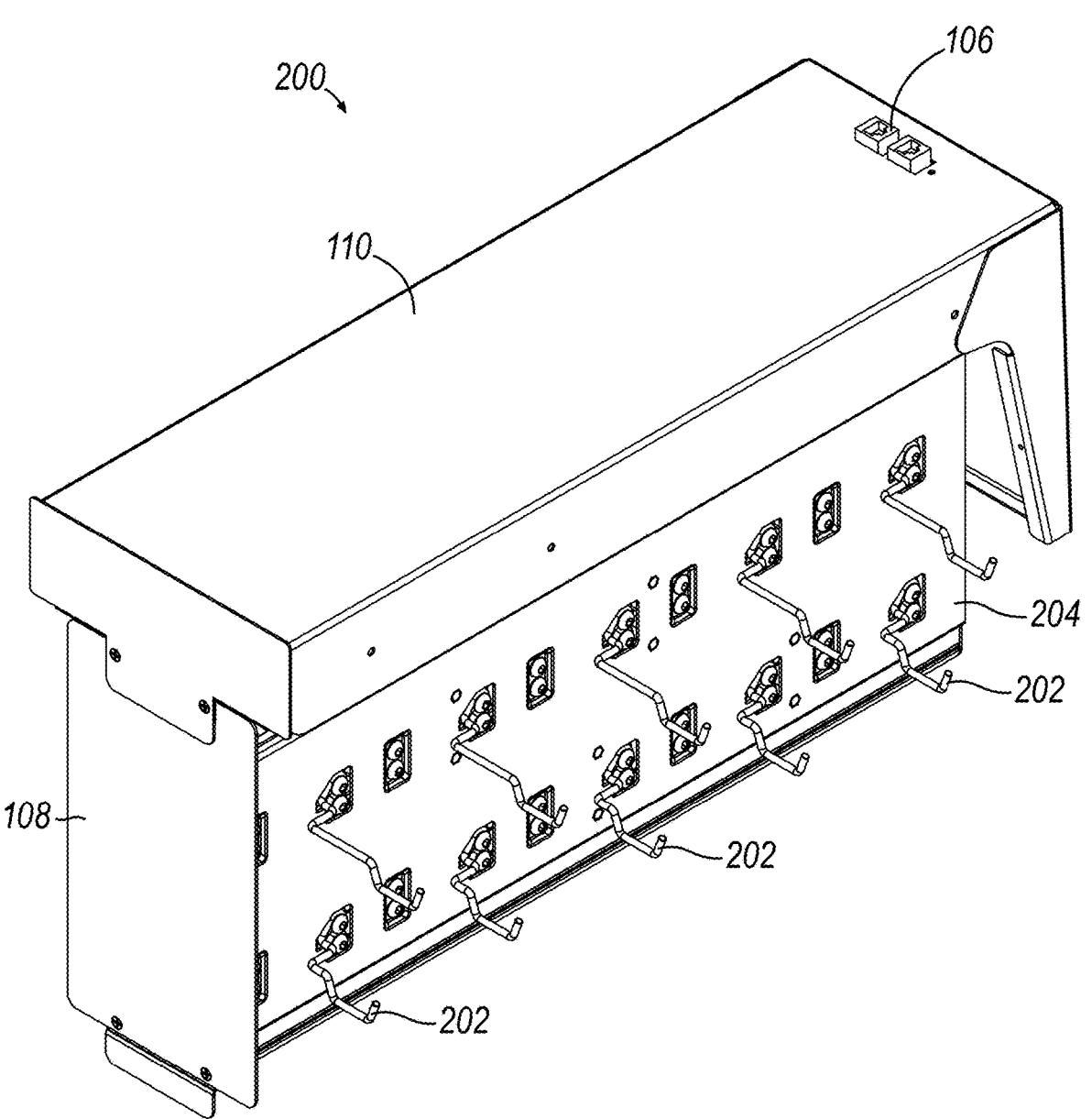
FIG. 2 is a perspective view of a catheter hanging system with a 20-scale configuration.

FIG. 2 shows a perspective view of a catheter hanging system (200) with a 20-scale configuration. Catheter hanging system (200) may be nearly identical to catheter system (100), except it includes 20 hooks (202) and 20 load cells instead of 12 hooks (102) and 12 load cells. Further, chassis (204) of catheter hanging system (200) may be configured to connect 20 hooks (202) and 20 load cells, as opposed to the smaller chassis (104).

Figure 3:
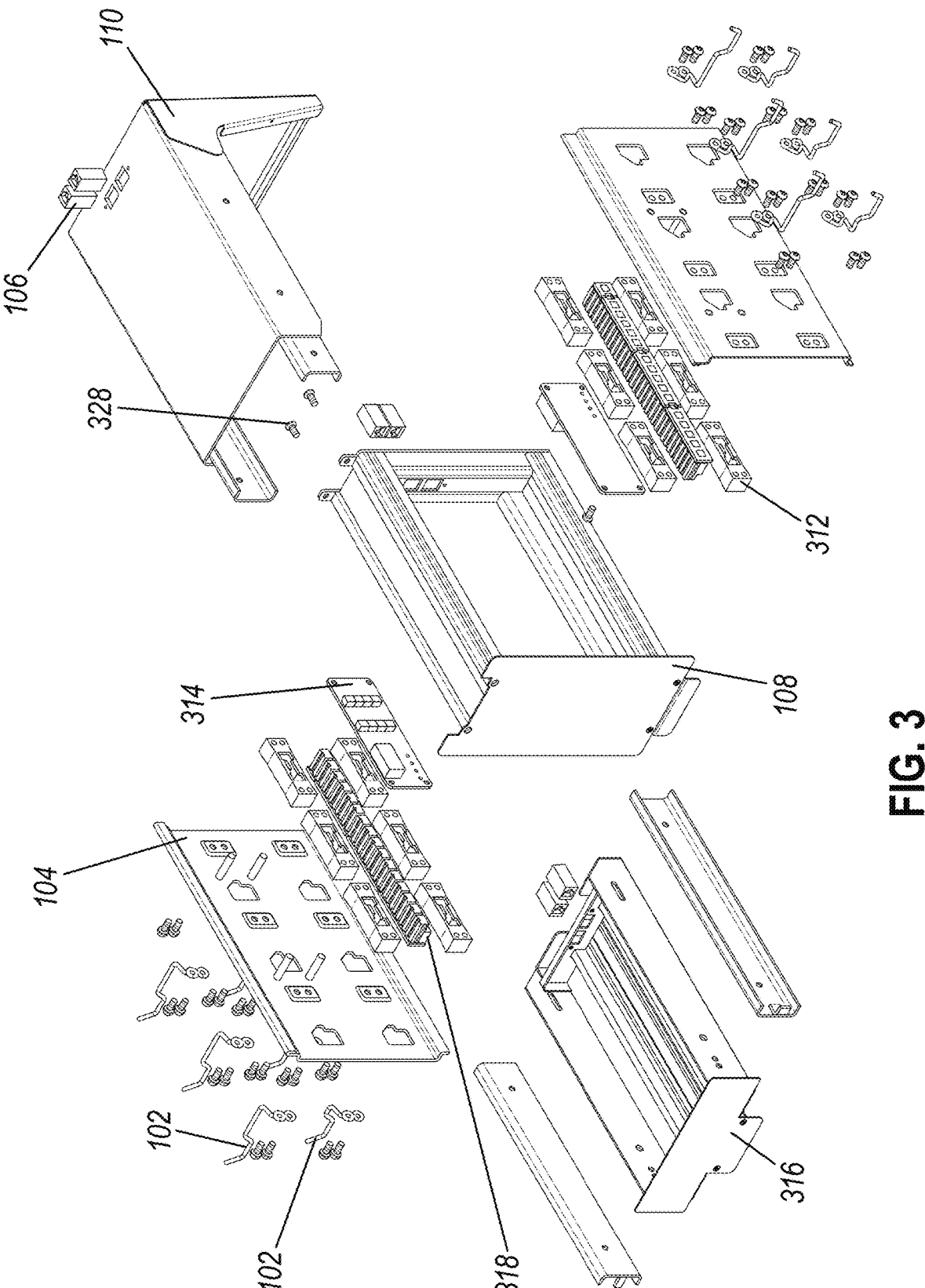
FIG. 3 is an exploded view of the catheter hanging system of FIG. 1.
Figure 4:
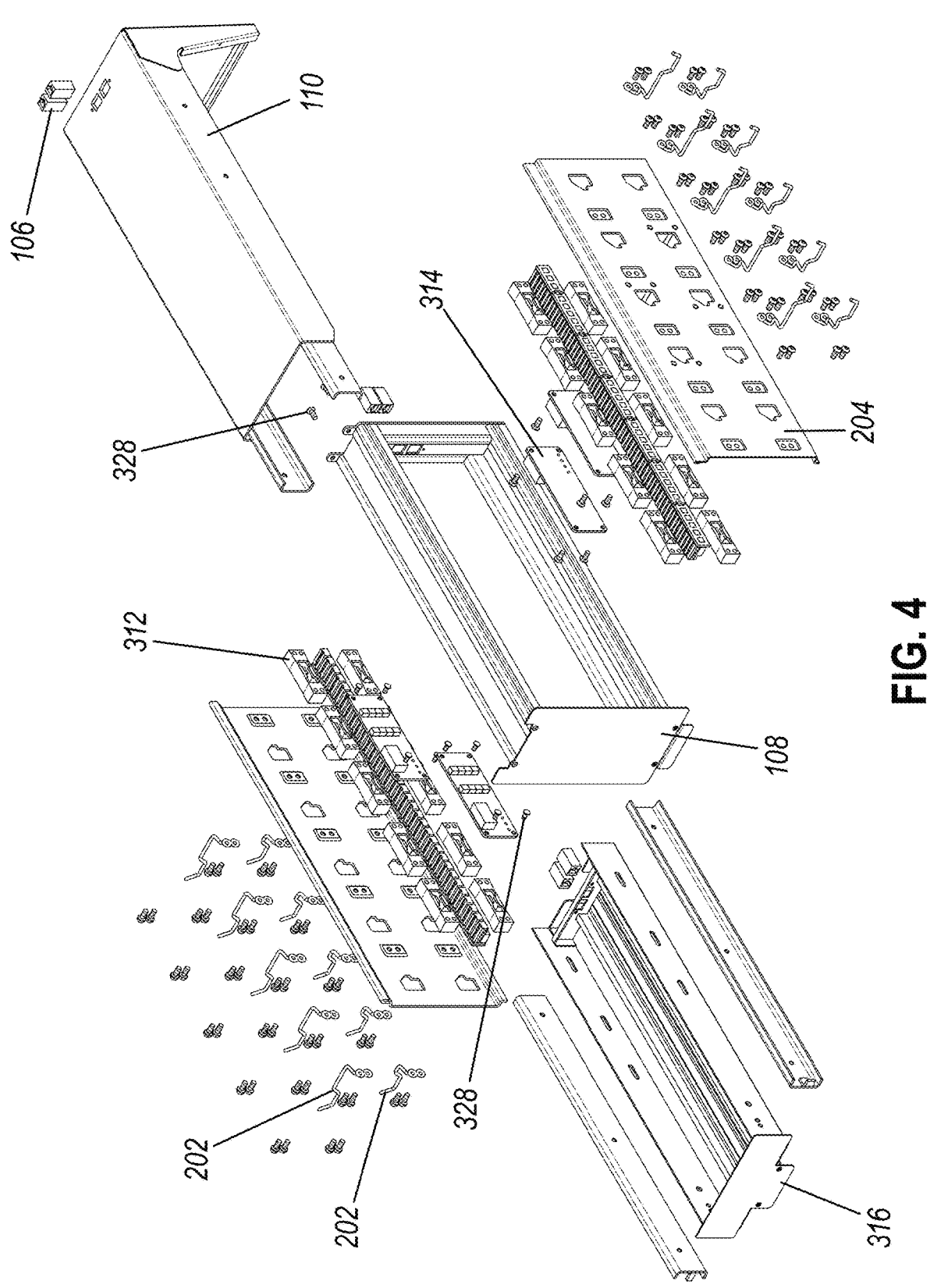
FIG. 4 is an exploded view of the catheter hanging system of FIG. 2.

FIG. 3 shows an exploded view of the catheter hanging system of FIG. 1. FIG. 4 shows an exploded view of the catheter hanging system of FIG. 2.

In one or more embodiments, catheter hanging system (100) includes a plurality of load cells (312) aligned with hooks (102). Load cells (312) are devices that convert weight into an electrical signal. In some embodiments, each individual load cell (312) may be connected to one hook (102) to continuously measure the weight of the medical inventory being weighed on hook (102).

Figure 5:
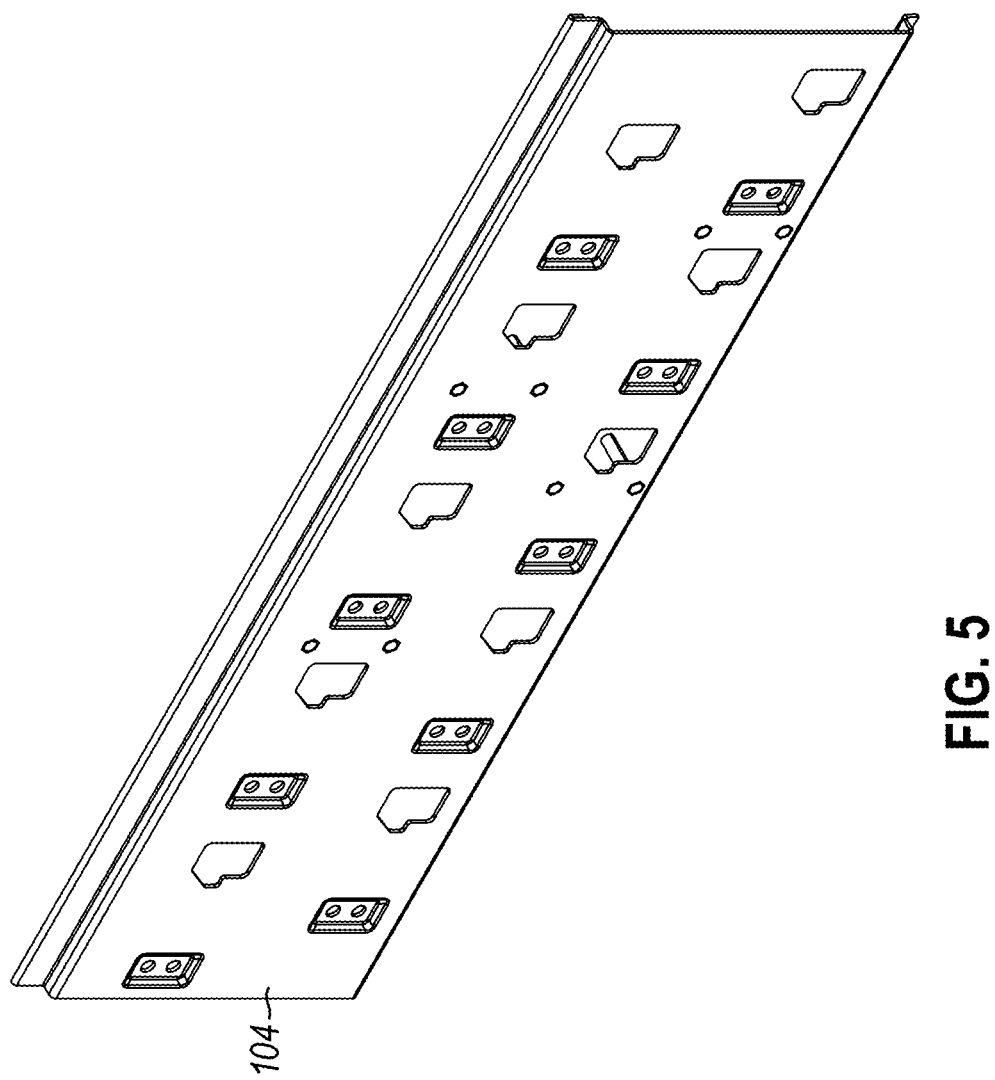
FIG. 5 is a perspective view of a chassis.

FIG. 5 shows a perspective view of chassis (104). Hooks (102) may be attached to a chassis (104) for support and to ensure safe, secure storage of catheters. In some examples, chassis (104) may be made of aluminum and provide support for the hooks (102) and load cells (312), thus allowing for each load cell (312) to be connected to its respective hook (102). Load cells (312) may be connected to the inside surface of chassis (104) with a connection mechanism, while hooks (102) are connected onto the outside surface of chassis (104). In some examples, the connection mechanism may be a plurality of screws. In other examples, the connection mechanism may be a plurality of louver hangers.

In one or more embodiments, catheter hanging system (100)/(200) further includes at least one circuit board (314). Circuit board (314) may be configured to automatically monitor the inventory being hung on hooks (102) and communicate information to a network (not shown), which can then be monitored by hospital personnel either via a display screen, desktop, or through a mobile application. Circuit board (314) may further connect with a controller (not shown). For instance, if catheter hanging system (100) has an error, such as measuring a negative weight or measuring a weight that does not correspond to a certain known number of catheters hanging on hook (102), then the controller may notify hospital staff or a third party.

For catheter hanging system (100), wherein there are 12 hooks and 12 load cells, chassis (104) may utilize two circuit boards. For catheter hanging system (200), wherein there are 20 hooks and 20 load cells, chassis (204) may utilize four circuit boards. Since traditional catheter hanging systems typically require one circuit board for every load cell, and thus would require 12 or 20 circuit boards for such configurations, the catheter hanging systems of the present disclosure are lighter, more efficient, and more cost-effective than those traditional catheter hanging systems. In some examples, catheter hanging system (100) may utilize one circuit board, and catheter hanging system (200) may utilize fewer than four circuit boards.

Circuit board (314) may further connect to a software interface that allows a user to log data, integrate the catheter hanging system with computer systems, or remotely monitor catheter hanging system (100)/(200). These functions allow a hospital to track inventory more efficiently and more accurately. For instance, a medical professional may be able to check the availability of a certain catheter without physically engaging with the storage unit system that the device may be kept in. Instead, the medical professional may check the catheter's availability from a computer that can be in another wing of the hospital, or from a mobile device such as a tablet.

In one or more embodiments, catheter hanging system (100)/(200) may include at least one coupler (106). At least one coupler (106) may be configured to facilitate communications between load cells (312) and circuit board (314). In some examples, coupler (106) may be used for Ethernet and other data transmission applications, providing a reliable and standardized connection for transmitting weight data from load cells (312) to circuit board (314). Further, coupler (106) allows for a modular and flexible design, allowing easy installation, maintenance and potential expansion of catheter hanging system (100). Coupler (106) allows for a communication network in which components can be connected and disconnected quickly and easily, thus enabling a medical professional to conveniently reconfigure or upgrade catheter hanging system (100) if needed.

Figure 6:
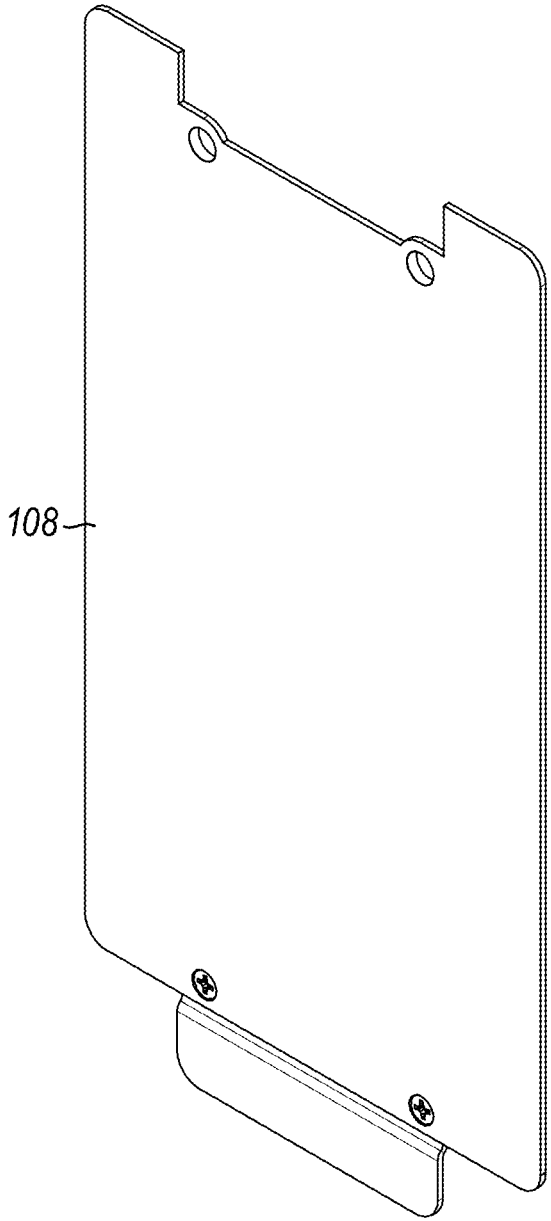
FIG. 6 is a perspective view of a slide assembly.

FIG. 6 shows a perspective view of a front plate (108). In one or more embodiments, catheter hanging system (100)/(200) may include front plate (108), configured to insulate the inventory of catheter hanging system (100). Front plate (108) may be a sheet of aluminum. Front plate (108) may be wide enough for readable labels that face forward, thereby allowing medical professionals to identify the inventory of catheter hanging system (100) without opening it. Catheter hanging system (100)/(200) may also include a top plate (110) that further insulates the inventory. In some examples, front plate (108) and top plate (110) may be attached to catheter hanging system (100)/(200) with screws (328).

Figure 7:
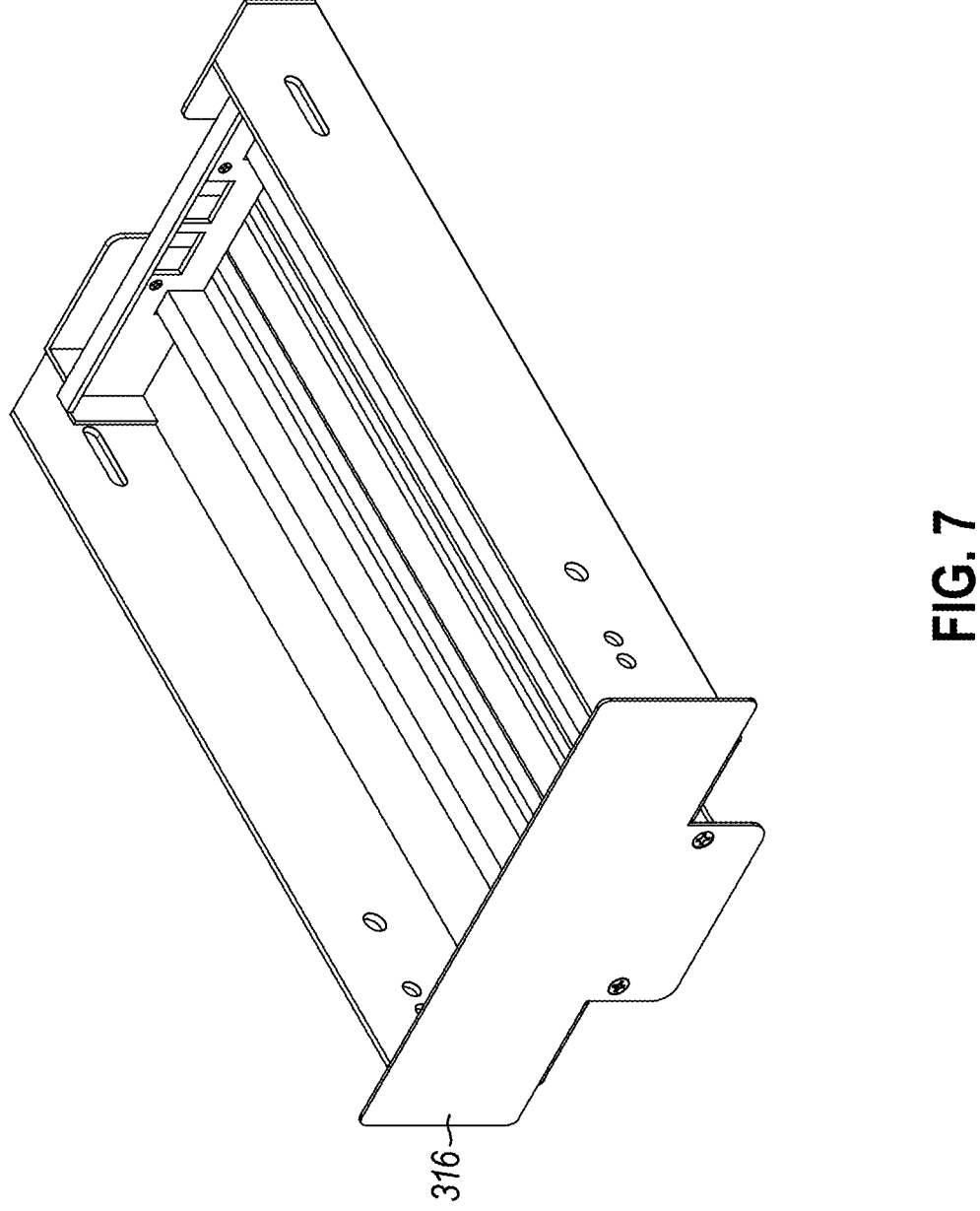
FIG. 7 is a perspective view of a front plate.

FIG. 7 shows a perspective view of a slide assembly (316). In one or more embodiments, catheter hanging system (100)/(200) may include slide assembly (316). In some embodiments, slide assembly (316) may be configured to slide catheter hanging system (100)/(200) open and closed, thereby allowing a medical professional to access the inventory when slid open, and secure the remaining inventory when slid shut.

In one or more embodiments, catheter hanging system (100)/(200) may further include a network of wiring (318) configured to connect load cells (312) to circuit board (314) and other electronic components of catheter hanging system (100)/(200). These connections made by network of wiring (318) facilitate easy assembly, disassembly, and maintenance of catheter hanging system (100). In some embodiments, network of wiring (318) may facilitate communication between load cells (312) and a software interface or controller. In some embodiments, network of wiring (318) may be connected to circuit board (314) with wire clips. In yet other embodiments, network of wiring (318) may be further secured with zip ties. In still other embodiments, network of wiring (318) may be further secured with an adhesive.

In one or more embodiments, catheter hanging system (100)/(200) may further include a digital display unit (not shown). The digital display unit may serve as an electronic label and may display electronic text for a medical professional to read. For example, an electronic label could display the total weight of the catheters being measured on plurality of hooks (102), or the number of catheters being stored on plurality of hooks (102), or the title of the instruments being stored on plurality of hooks (102). A digital display unit may further include a plurality of buttons or controls for operation.

In one or more embodiments, catheter hanging system (100)/(200) of the present disclosure may further include a control panel (not shown). In some catheter hanging systems of the present disclosure, there may be a separate control panel for configuring settings, calibrating load cells (312), or accessing additional features.

In some embodiments, catheter hanging system (100)/(200) may include one or more load cells (312) that are configured in tandem together. In such embodiments, two or more load cells (312) would connect together to measure the weight applied to a single hook (102). This setup may allow for more accurate and reliable weight measurement, especially when heavier inventory may be hung from hooks (102). Further, since load cells (312) of the present disclosure are interchangeable, the ability to tandem one or more load cells (312) together provides medical professionals the versatility of customizing catheter hanging system (100)/(200) according to specific needs or allows medical professionals to adjust for the type of inventory being stored.

In yet other embodiments, load cells (312) may be connected with a wireless connection, such as Bluetooth, instead of with network of wires (318). Such embodiments may include a battery to power load cells (312), thus removing network of wires (318). A wireless system of load cells (312) may be most useful in environments with a lower risk of connection issues than a hospital floor, such as a warehouse, clinical building, or a hospital basement.

In one or more embodiments, catheter hanging system (100)/(200) may include an illuminator (not shown) configured to activate and light up if certain conditions are met. For instance, the illuminator may light up the catheter hanging system (100)/(200) that has a hook with a catheter that a nurse needs to retrieve, or the catheter hanging system (100)/(200) that may be experiencing an error. The illuminator may flash different flash rates or different colors to communicate different messages to hospital staff.

II. Catheter Hanging System with a Telescopic Apparatus

In some embodiments, the catheter hanging system of the present disclosure may include a telescopic apparatus. A telescopic apparatus can be a versatile apparatus designed with sections that can extend and retract, providing adjustable length and compatibility. The telescopic apparatus may consist of nested rectangular tubes, with one section sliding inside another. This design may allow for medical professionals to easily extend the frame to its full length to retrieve catheters from hooks, and then retract it back to its compact form for storage. In some examples, the telescopic apparatus operates through a system of interlocking grooves. As discussed in further detail below, a catheter hanging system with a telescopic apparatus may have hooks attached to and hanging down from the outside of the bottom surface of the telescopic apparatus, while load cells may be secured on the inside of the telescopic apparatus.

Figure 8A:
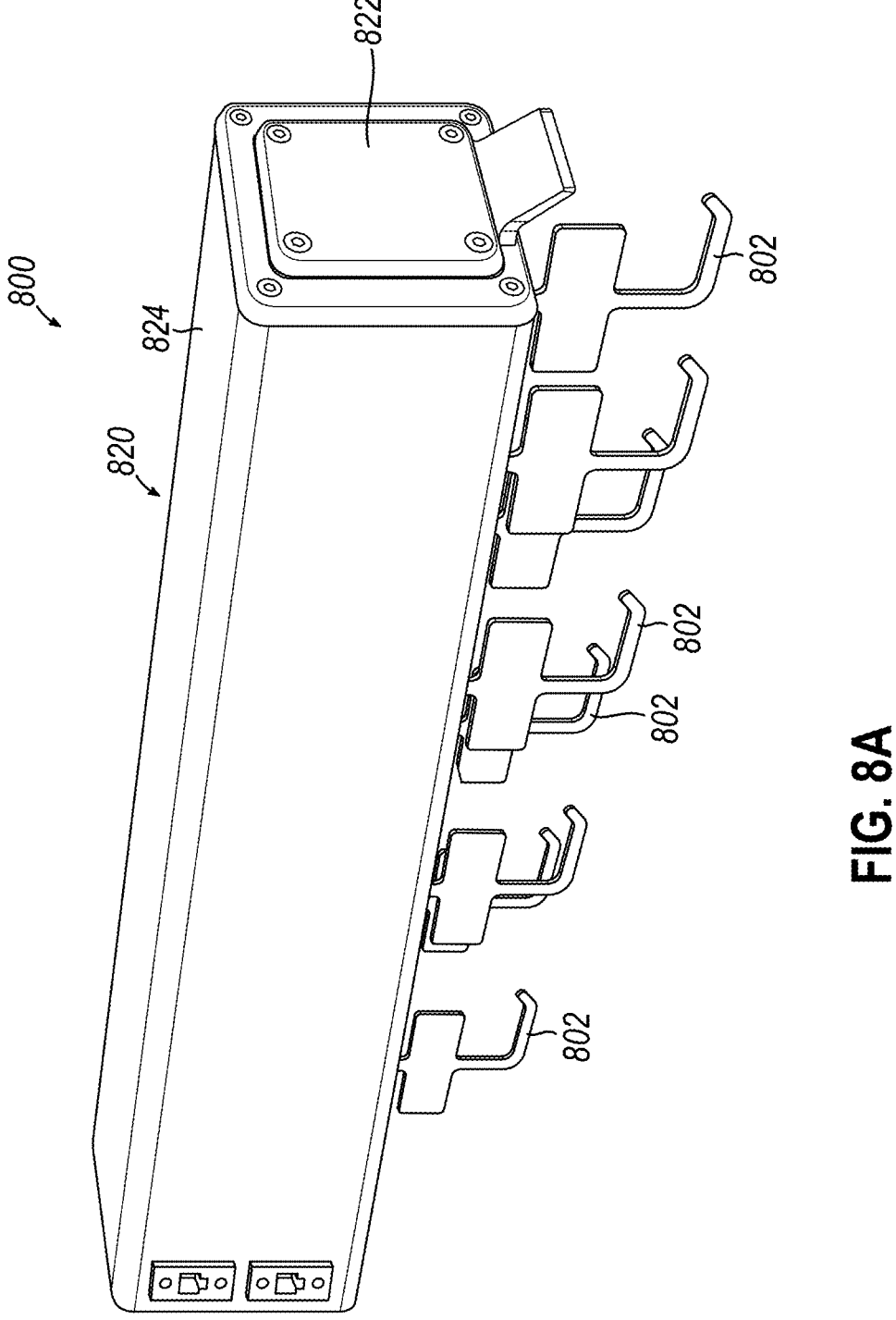
FIG. 8A is a perspective view of a catheter hanging system with a telescopic apparatus in a retracted position.
Figure 8B:
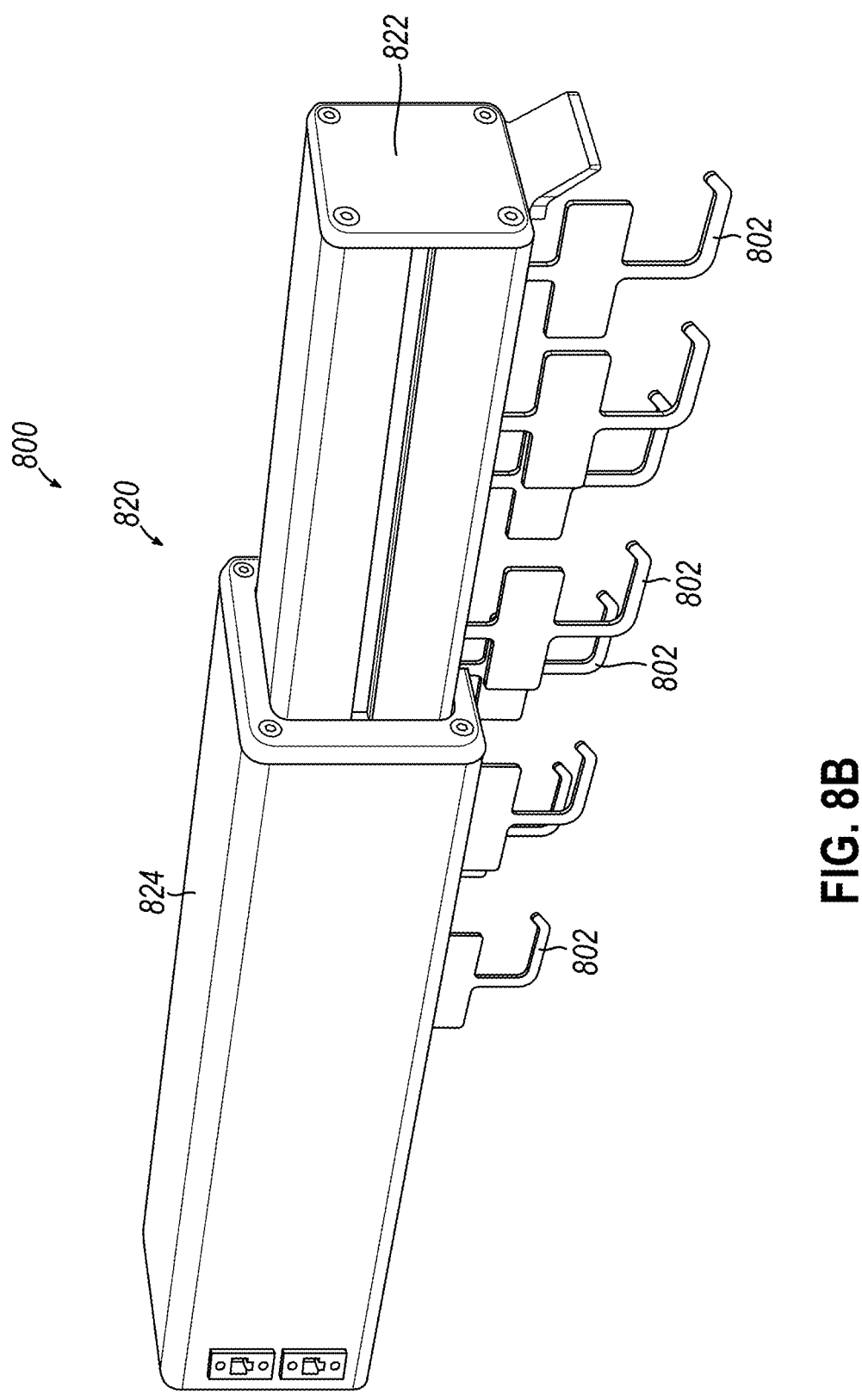
FIG. 8B is a perspective view of the catheter hanging system of FIG. 8A with the telescopic apparatus in the extended position.

FIG. 8A shows a perspective view of a catheter hanging system (800) that includes a telescopic apparatus (820) in a retracted position. FIG. 8B shows a perspective view of catheter hanging system (800) of FIG. 8A with telescopic apparatus (820) in an extended position. Telescopic apparatus (820) may include an inner frame (822), which may be nested within an outer frame (824). In some examples, inner frame (822) is not nested within outer frame (824). Inner frame (822) may be configured to slide out of outer frame (824) into an extended position and slide back into outer frame (824) into a retracted position.

In such an embodiment, hooks (802) of catheter hanging system (800) may be attached to the outside of the bottom surface of inner frame (822), such that catheters hang directly below inner frame (822). In one example, hooks (802) may be placed in a straight line, such that each hook (802) may be aligned with the hooks (802) adjacent to it. In other examples, hooks (802) may be staggered, such that there are two rows of hooks (802), and each hook (802) may not be directly aligned with the adjacent hook (802), such that the arrangement of hooks (802) forms a zig-zag pattern. The configuration of hooks (802) may be changed and can be flexible based on the size of the catheters being stored and the needs of the medical facility.

Figure 9:
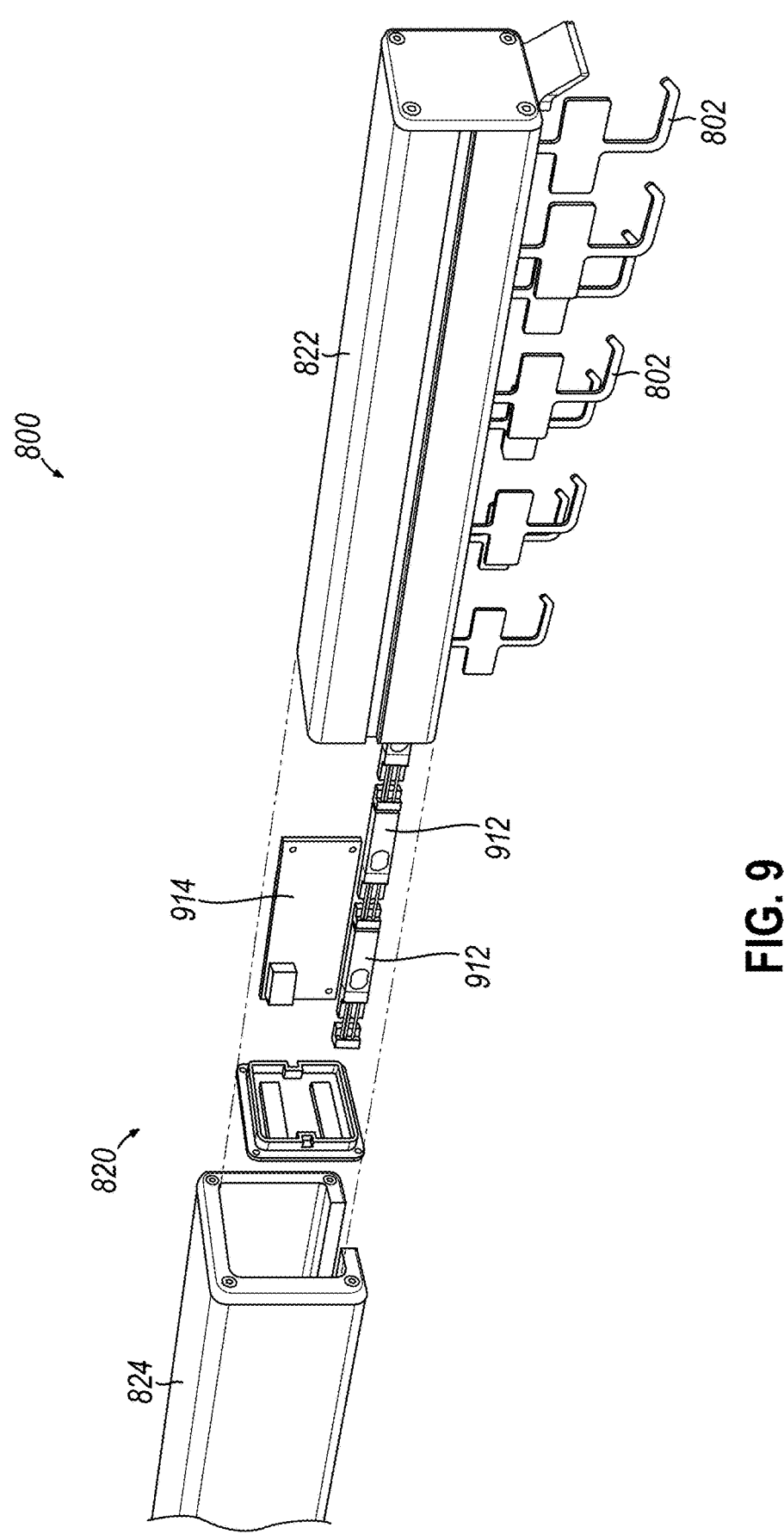
FIG. 9 is an exploded view of the catheter hanging system of FIG. 8A.

FIG. 9 shows an exploded view of catheter hanging system (800). In some embodiments, load cells (912) and circuit board (914) are positioned within telescopic apparatus (920). Load cells (912) may rest on top of the bottom surface of inner frame (822), in order to be in proximity with hooks (802) which are hanging vertically down from the bottom of the bottom surface of inner frame (824). In such embodiments, load cells (912) may be configured to be attached to hooks (802) with telescopic apparatus (820) in a retracted position and may be detached from hooks (802) with telescopic apparatus (820) in an extended position.

Figure 10:
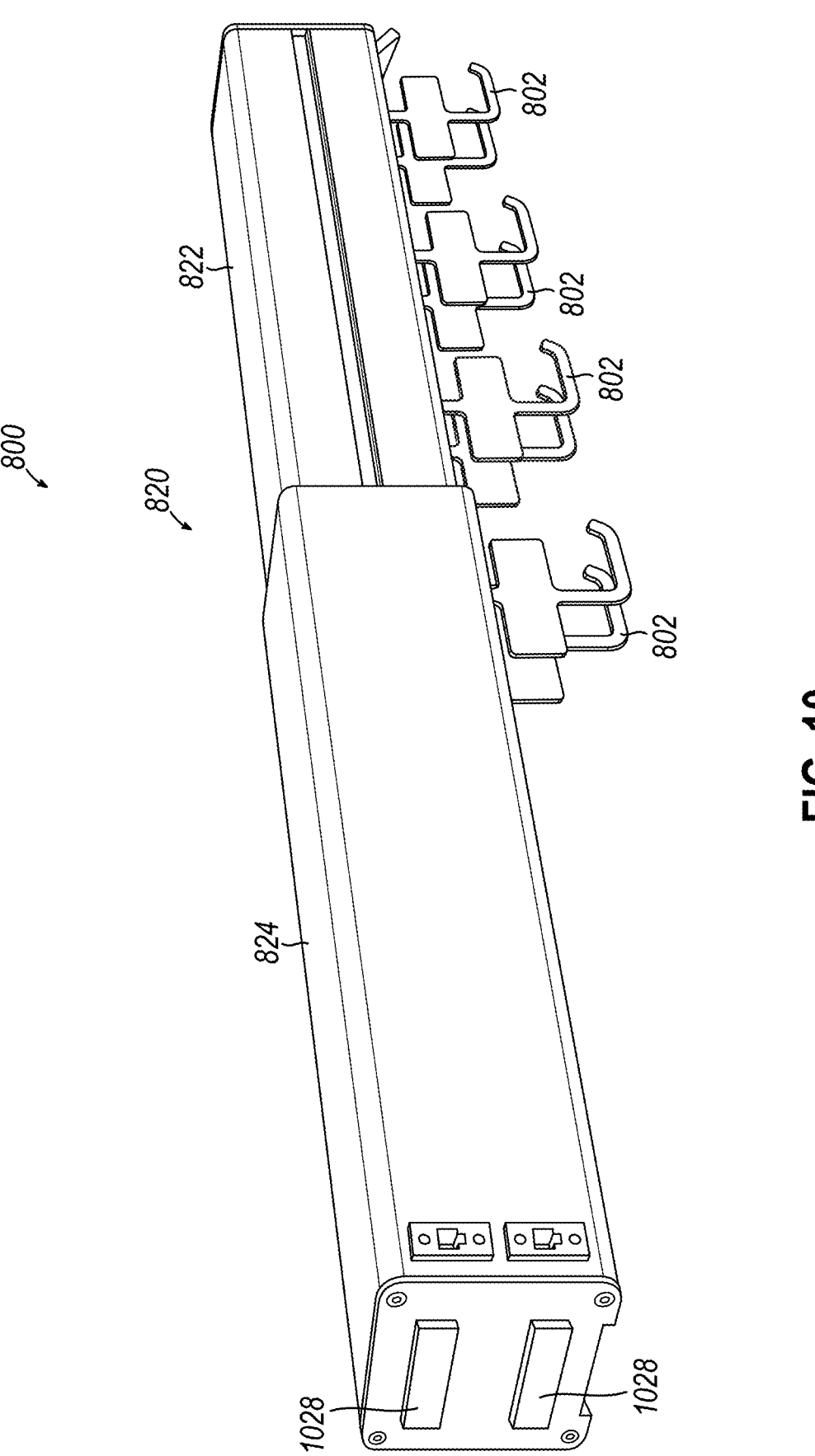
FIG. 10 is a perspective view of the catheter hanging system of FIG. 8A including a mounting bracket.
Figure 11:
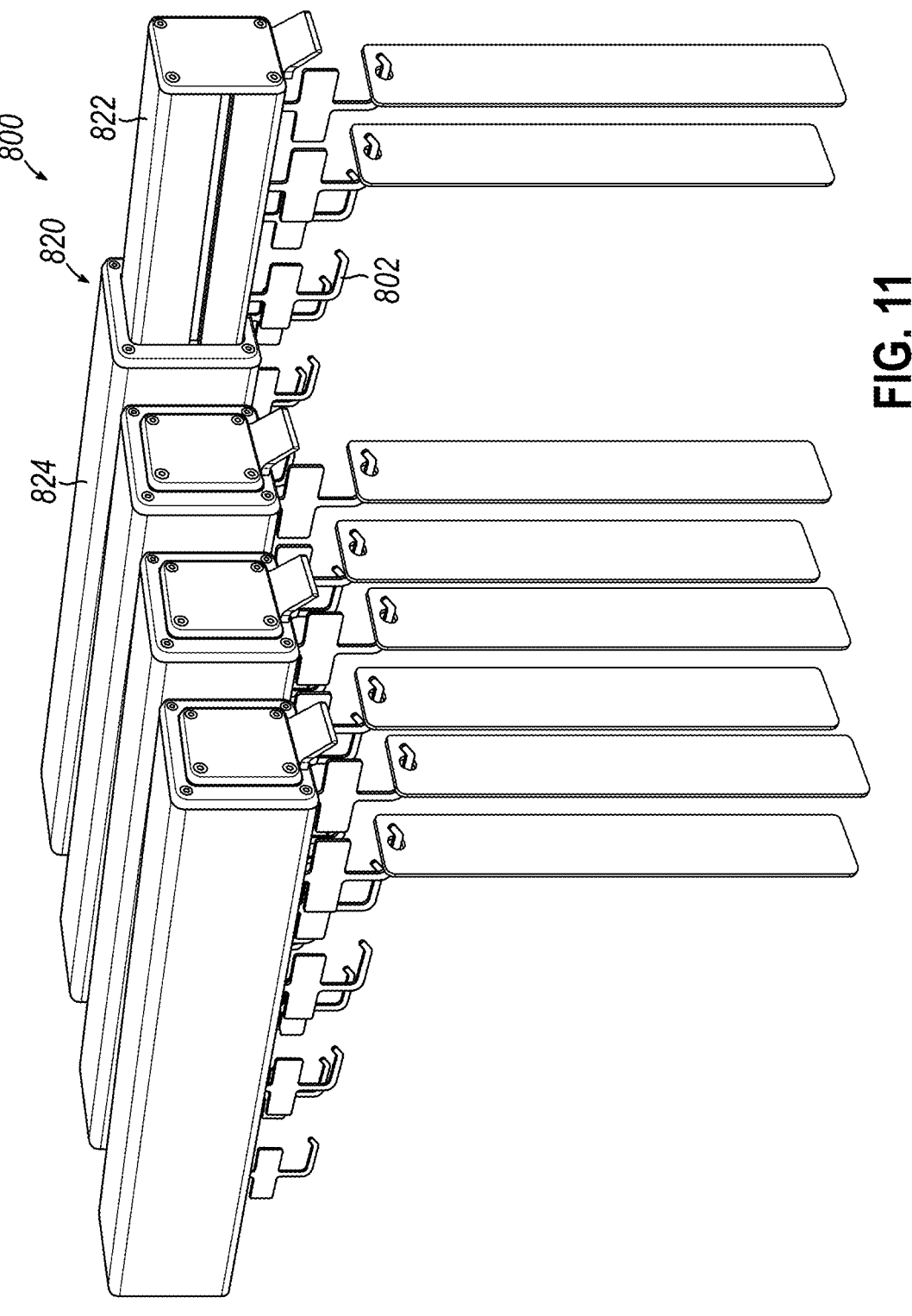
FIG. 11 is a perspective view of multiple catheter systems of FIG. 8A mounted to a wall of a storage unit system.

FIG. 10 shows catheter hanging system (800) of FIG. 9 with a mounting bracket (1028). FIG. 11 shows catheter hanging system (800) of FIG. 9 in use and mounted on a wall of a storage unit system. In some embodiments, catheter hanging system (800) may include mounting bracket (1028) configured to install catheter hanging system (800) in a variety of storage unit systems. For instance, while other catheter hanging systems are fixed in the storage unit systems they were created for, catheter hanging system (800) of the present disclosure may be installed in a cabinet storage unit, onto a rack storage system, on louvers on a wall, or on the ceiling of a storage unit system. Further, catheter hanging system (800) may be installed into a cabinet storage unit of a particular brand, and later may be removed from that cabinet and then installed into a different cabinet storage unit of a different brand. In this way, catheter hanging system (800) may be retrofit to accommodate a wide variety of storage unit systems. This scalability may give a hospital more flexibility when storing various catheters. It may also save a hospital money by allowing them to replace a catheter hanging system without replacing an entire storage unit system.

III. Exemplary Combinations

Example 1

A catheter hanging system including: (a) a plurality of hooks; (b) a plurality of load cells, wherein each load cell of the plurality of load cells is configured to continuously measure a weight applied to one of the hooks; and (c) at least one circuit board configured to receive signals from the plurality of load cells.

Example 2

The catheter hanging system of Example 1, further including a chassis configured to support the plurality of hooks and plurality of load cells in a structured arrangement.

Example 3

The catheter hanging system of Example 1, further including a slide assembly configured to slide the catheter hanging system into an open position or closed position.

Example 4

The catheter hanging system of Example 1, further including a front plate configured to insulate the catheter hanging system.

Example 5

The catheter hanging system of Example 1, further including a network of wiring configured to connect the plurality of hooks, plurality of load cells, and circuit board.

Example 6

The catheter hanging system of Example 1, wherein the plurality of hooks includes at least 12 hooks and two or fewer circuit boards.

Example 7

The catheter hanging system of Example 1, wherein the plurality of hooks includes 20 hooks and four or fewer circuit boards.

Example 8

The catheter hanging system of Example 1, wherein each load cell of the plurality of load cells is configured such that multiple load cells may be connected in tandem to measure the weight of at least one hook.

Example 9

The catheter hanging system of Example 1, wherein the circuit board is configured to provide real-time monitoring of inventory.

Example 10

The catheter hanging system of Example 1, further including a display screen.

Example 11

A catheter hanging system including: (a) a plurality of hooks; (b) a plurality of load cells, wherein each load cell of the plurality of load cells is configured to continuously measure a weight applied to one of the hooks; (c) at least one circuit board configured to receive signals from the plurality of load cells; (d) a chassis configured to support the plurality of hooks and plurality of load cells in a structured arrangement; (e) a slide assembly configured to slide the catheter hanging system into an open or closed position; and (f) a front plate configured to insulate the catheter hanging system.

Example 12

A catheter hanging system including: (a) a plurality of hooks; (b) a plurality of load cells, wherein each load cell of the plurality of load cells is configured to continuously measure a weight applied to one of the hooks; (c) at least one circuit board configured to receive signals from the plurality of load cells; (d) a telescopic apparatus, wherein the plurality of hooks is attached to the telescopic apparatus, wherein the telescopic apparatus is configured to slide out to an extended position and slide in to a retracted position; and (f) a mounting bracket configured to attach the catheter hanging system to a storage unit system.

Example 13

The catheter hanging system of Example 12, wherein each hook of the plurality of hooks is attached to a bottom surface of the telescopic apparatus.

Example 14

The catheter hanging system of Example 12, wherein each hook of the plurality of hooks is aligned in a straight line, such that each hook of the plurality of hooks is directly in front of the adjacent hooks.

Example 15

The catheter hanging system of Example 12, wherein each hook of the plurality of hooks is aligned in a staggered arrangement, such that each hook of the plurality of hooks is not directly in front of the adjacent hooks.

Example 16

The catheter hanging system of Example 12, wherein each load cell of the plurality of load cells is located within the telescopic apparatus.

Example 17

The catheter hanging system of Example 12, wherein each load cell of the plurality of load cells is configured to be attached to the plurality of hooks when the telescopic apparatus is in the retracted position, and wherein each load cell of the plurality of load cells is configured to be detachable from the plurality of hooks when the telescopic apparatus is in the extended position.

Example 18

The catheter hanging system of Example 12, wherein the mounting bracket is configured to attach the catheter hanging system to a wall of a storage unit system.

Example 19

The catheter hanging system of Example 12, wherein the mounting bracket is configured to attach the catheter hanging system to a ceiling of a storage unit system.

Example 20

The catheter hanging system of Example 20, wherein the telescopic apparatus includes: (a) an outer frame; and (b) an inner frame configured to extend out of the outer frame and retract into the outer frame.

V. Conclusion

It should be understood that any one or more of the teachings, embodiments, examples, etc. described herein may be combined with any one or more of the other teachings, embodiments, examples, etc. that are described herein. The following-described teachings, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Having shown and described various examples of the present disclosure, further adaptations of the methods and systems described herein may be accomplished by appropriate modifications by one of ordinary skill in the art without departing from the scope of the present disclosure. Accordingly, the scope of the present disclosure should be considered in terms of the following claims and is understood not to be limited to the details of structure and operation shown and described in the specification and drawings.

We claim:

1. A catheter hanging system including:
(a) a plurality of hooks;
(b) a plurality of load cells, wherein each load cell of the plurality of load cells is configured to continuously measure a weight applied to one of the hooks of the plurality of hooks;
(c) at least one circuit board configured to receive signals from the plurality of load cells; and
(d) a telescopic apparatus including an outer frame and an inner frame configured to slidably extend out of the outer frame and retract into the outer frame, wherein each hook of the plurality of hooks is attached to a bottom surface of the inner frame of the telescopic apparatus, wherein each load cell of the plurality of load cells is disposed within the telescopic apparatus and supported by the inner frame, wherein the telescopic apparatus is configured to slide out to an extended state and slide into a retracted state such that the plurality of load cells are positioned above the plurality of hooks when the telescopic apparatus is in the retracted state, and wherein the plurality of load cells and plurality of hooks are configured to continuously measure the weight when the telescopic apparatus is in the retracted state and disengage when the telescopic apparatus is in the extended state.

2. The catheter hanging system of claim 1, further including a network of wiring configured to connect the plurality of hooks, plurality of load cells, and the at least one circuit board.

3. The catheter hanging system of claim 1, wherein each load cell of the plurality of load cells is configured such that multiple load cells of the plurality of load cells may be connected in tandem to measure the weight of one hook of the plurality of hooks.

4. The catheter hanging system of claim 1, wherein the at least one circuit board is configured to provide real-time monitoring of inventory.

5. The catheter hanging system of claim 1, further including a display screen.

6. A catheter hanging system including:
(a) a plurality of hooks;
(b) a plurality of load cells, wherein each load cell of the plurality of load cells is configured to continuously measure a weight applied to one of the hooks of the plurality of hooks;
(c) at least one circuit board configured to receive signals from the plurality of load cells;
(d) a telescopic apparatus including an outer frame and an inner frame configured to slidably extend out of the outer frame and retract into the outer frame, wherein each hook of the plurality of hooks is attached to a bottom surface of the inner frame of the telescopic apparatus, wherein each load cell of the plurality of load cells is disposed within the telescopic apparatus and supported by the inner frame, wherein the telescopic apparatus is configured to slide out to an extended state and slide into a retracted state such that the plurality of load cells are positioned above the plurality of hooks when the telescopic apparatus is in the retracted state, and wherein the plurality of load cells and plurality of hooks are configured to continuously measure the weight when the telescopic apparatus is in the retracted state and disengage when the telescopic apparatus is in the extended state; and
(e) a mounting bracket configured to attach the catheter hanging system to a storage unit system.

7. The catheter hanging system of claim 6, wherein each hook of the plurality of hooks is aligned in a straight line, such that each hook of the plurality of hooks is directly in front of adjacent hooks.

8. The catheter hanging system of claim 6, wherein each hook of the plurality of hooks is aligned in a staggered arrangement, such that each hook of the plurality of hooks is not directly in front of adjacent hooks.

9. The catheter hanging system of claim 6, wherein each load cell of the plurality of load cells is configured to engage the plurality of hooks for weight measurement when the telescopic apparatus is in the retracted position, and wherein extension of the telescopic apparatus causes separation between the plurality of load cells and plurality of hooks sufficient to prevent weight measurement.

10. The catheter hanging system of claim 6, wherein the mounting bracket is configured to attach the catheter hanging system to a wall of a storage unit system.

11. The catheter hanging system of claim 6, wherein the mounting bracket is configured to attach the catheter hanging system to a ceiling of a storage unit system.

* * * * *